(12) United States Patent
Davis et al.

(10) Patent No.: US 7,163,696 B2
(45) Date of Patent: Jan. 16, 2007

(54) PHARMACEUTICAL FORMULATIONS

(75) Inventors: John Douglas Davis, Sandwich (GB); Michael John Humphrey, Sandwich (GB); Ross James Macrae, Sandwich (GB); Janet Sarah Smith, Sandwich (GB)

(73) Assignee: Pfizer Inc., New York, NY (US)

( * ) Notice: Subject to any disclaimer, the term of this patent is extended or adjusted under 35 U.S.C. 154(b) by 543 days.

(21) Appl. No.: 10/269,551

(22) Filed: Oct. 10, 2002

(65) Prior Publication Data

US 2003/0133978 A1    Jul. 17, 2003

Related U.S. Application Data

(60) Provisional application No. 60/340,717, filed on Oct. 30, 2001.

(30) Foreign Application Priority Data

Oct. 11, 2001  (GB)  ................................ 0124455.7

(51) Int. Cl.
  *A61K 9/14*  (2006.01)
  *A61K 9/18*  (2006.01)
  *A61K 9/26*  (2006.01)

(52) U.S. Cl. ...................... 424/486; 424/469; 424/480; 424/493; 424/499

(58) Field of Classification Search ................ 424/468, 424/469, 470, 472, 473, 474, 475, 480, 476, 424/482, 484
See application file for complete search history.

(56) References Cited

U.S. PATENT DOCUMENTS 6,106,864 A * 8/2000 Dolan et al. ................. 424/488
6,149,940 A   11/2000 Maggi et al. ................ 424/472
6,596,900 B1 * 7/2003 Blakemore et al. ......... 562/501

FOREIGN PATENT DOCUMENTS

| EP | 0466986 | 1/1992 |
|----|---------|--------|
| EP | 1123705 | 8/2001 |
| WO | WO9830560 | 7/1998 |
| WO | WO0164672 | 9/2001 |

* cited by examiner

*Primary Examiner*—Jyothsna Venkat
(74) *Attorney, Agent, or Firm*—Gregg C. Benson; Carl J. Goddard (57) ABSTRACT

The invention provides a controlled-release pharmaceutical formulation for oral administration comprising 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof; and a pharmaceutically acceptable adjuvant, diluent or carrier; characterized in that the formulation is adapted to release at least 50% by weight of the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, after 6 hours in Apparatus 1 described in the United States Pharmacopoeia 24 (2000), pp 1941–1943, having 1 litre vessels, baskets of 40 mesh (0.4 mm apertures), a rotation speed of 100 rpm, and a dissolution medium consisting of 900 ml of 0.01 M hydrochloric acid containing 0.7% w/v sodium chloride at 37° C.

Formulations according to the invention are suitable for the treatment of BPH.

11 Claims, 1 Drawing Sheet

PHARMACEUTICAL FORMULATIONS

This application is filed claiming priority to co-pending U.S. Provisional Application No. 60/340,717, filed Oct. 30, 2001, and GB Provisional Application No. 0124455.7, filed Oct. 11, 2001.

This invention relates to controlled-release oral pharmaceutical formulations of α adrenergic receptor antagonist compounds, including 4-amino-6,7-dimethoxy-2-(5-methanesulfonamido-1,2,3,4-tetrahydroisoquinol-2-yl)-5-(2-pyridyl)quinazoline and pharmaceutically acceptable salts thereof.

Controlled-release oral pharmaceutical formulations are known. Their purpose is to modify the rate of drug release, for example to produce a constant rate of release of a drug into the gastrointestinal tract of a patient, or to delay the release of a drug into the gastrointestinal tract of a patient (see Gupta and Robinson, "Oral controlled release delivery", Chapter 6 in: Treatise on Controlled Drug Delivery, Editor A. Kydonieus, Dekker, N.Y., 1992).

Streubel et al (Journal of Controlled Release, 67 (2000) p101–110) disclose tablets of verapamil hydrochloride containing hydroxypropylmethyl cellulose and organic acids.

Many α adrenergic receptor antagonist compounds have been described. They have been indicated in the treatment of hypertension, congestive heart failure, benign prostatic hyperplasia (BPH) and Raynaud's Syndrome. Prazosin and alfuzosin are examples of α adrenergic receptor antagonist compounds, and controlled-release formulations of them are disclosed in International Patent Application WO 94/27582.

The treatment of BPH is of particular interest, and formulations containing antagonist compounds selective for the $\alpha_1$ adrenergic receptor, especially the $\alpha_{1A}$ subtype (formerly known as the $\alpha_{1C}$ subtype) are of particular interest. Such a compound is 4-amino-6,7-dimethoxy-2-(5-methanesulfonamido-1,2,3,4-tetrahydroisoquinol-2-yl)-5-(2-pyridyl) quinazoline, and its pharmaceutically acceptable salts.

4-Amino-6,7-dimethoxy-2-(5-methanesulfonamido-1,2,3,4-tetrahydroisoquinol-2-yl)-5-(2-pyridyl(quinazoline, and its pharmaceutically acceptable salts, are disclosed in International Patent Application WO 98/30560 (see in particular Example 19). The mesylate salt of the compound is disclosed in WO 01/64672 (e.g. see Example 2). Both WO 98/30560 and WO 01/64672 are incorporated herein by reference.

4-Amino-6,7-dimethoxy-2-(5-methanesulfonamido-1,2,3,4-tetrahydroisoquinol-2-yl)-5-(2-pyridyl)quinazoline, and its pharmaceutically acceptable salts, are indicated in the treatment of benign prostatic hyperplasia. The free base has the following structure:

A problem that can arise in the oral administration of α adrenergic receptor antagonist compounds is poor or unpredictable absorption of the compound from the gastrointestinal tract. Another problem that can arise is sudden drops in blood pressure, particularly when the drug is released too rapidly into the gastrointestinal tract. In WO 94/27582, the first problem was addressed by formulating the α adrenergic receptor antagonist compounds alfuzosin and prazosin so as to give a biphasic release profile. Release of the drugs in two portions was preferred, with the preferred ratio of the two portions being 3:7, so that a high concentration could be maintained in the colon, where absorption of the drugs was found to be poor.

Bioavailability testing of 4-amino-6,7-dimethoxy-2-(5-methanesulfonamido-1,2,3,4-tetrahydroisoquinol-2-yl)-5-(2-pyridyl)quinazoline, and its pharmaceutically acceptable salts, by the applicants (unpublished), gave surprising results in that absorption from the colon was found to be low, and highly variable. It was unexpectedly found that intersubject variability could be minimized by administering 4-amino-6,7-dimethoxy-2-(5-methanesulfonamido-1,2,3,4-tetrahydroisoquinol-2-yl)-5-(2-pyridyl)quinazoline, and its pharmaceutically acceptable salts, in a controlled-release dosage form which delivered the majority of the drug to the upper gastrointestinal tract. Surprisingly, unacceptable sudden drops in blood pressure were not observed, and yet blood concentrations in vivo were sufficiently sustained to allow once daily dosing.

Therefore, according to the present invention, there is provided a controlled-release pharmaceutical formulation for oral administration comprising 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof; and a pharmaceutically acceptable adjuvant, diluent or carrier; characterized in that the formulation is adapted to release at least 50% by weight of the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, after 6 hours in Apparatus 1 described in the United States Pharmacopoeia 24 (2000), pp 1941–1943, having 1 litre vessels, baskets of 40 mesh (0.4 mm apertures), a rotation speed of 100 rpm, and a dissolution medium consisting of 900 ml of 0.01 M hydrochloric acid containing 0.7% w/v sodium chloride at 37° C.

The dissolution apparatus and conditions mentioned above are believed to model the conditions in the upper gastrointestinal tract. By "upper gastrointestinal tract" is meant the portion of the gastrointestinal tract between the mouth and the ileo-caecal junction inclusive. Furthermore, the time taken for a swallowed item to reach the ileo-caecal junction and pass into the lower gastrointestinal tract is thought to be about 6 hours (see the lecture by Professor Sidney Phillips entitled 'Gastrointestinal physiology and its relevance to targeted drug delivery', given 22 Apr. 1993 in Short Hills (New Jersey, USA) as part of the Capsugel Symposia series 'Current status on targeted drug delivery to the gastrointestinal tract', subsequently published as part of the Capsugel Library).

Therefore, the invention may be stated alternatively as a controlled-release pharmaceutical formulation for oral administration comprising 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof; and a pharmaceutically acceptable adjuvant, diluent or carrier; characterized in that the formulation is adapted to release at least 50% by weight of the 4-amino- 6,7-dimethoxy-2-(5-methanesulfonamido-1,2,3,4-tetrahydroisoquinol-2-yl)-5-(2-pyridyl)quinazoline, or the pharmaceutically acceptable salt thereof, in the upper gastrointestinal tract of a patient.

Preferably, at least 30% by weight of the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, is released after 3 hours in the dissolution apparatus (or following ingestion).

Preferably, less than 30% by weight of the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, is released after 1 hour in the dissolution apparatus (or following ingestion).

Preferably, formulations according to the invention contain from 0.1 mg to 20 mg (for example 1 to 15 mg) of 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof. It is preferred that such formulations are administered once a day to human patients.

In formulations according to the present invention, it is preferred that the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, in said dosage form is:

(a) embedded in a matrix from which it is released by diffusion or erosion;
(b) present in a multiparticulate core (sometimes referred to as a bead formulation);
(c) released through an aperture provided in an impermeable coating (sometimes referred to as an osmotic formulation);
(d) released through a coating of low aqueous solubility;
(e) released through a semipermeable coating;
(f) present as an ion exchange resin; or
(g) released at specific points in the gastrointestinal tract by a pulsatile device.

Matrix, bead and osmotic formulations are of interest. Dealing with each category in turn:

(a) In matrix systems, the active compound is embedded or dispersed in a matrix of another material which serves to retard the release of the active compound into an aqueous environment. Suitable matrix materials include hydroxypropyl methylcellulose and hydroxypropyl cellulose. Matrix formulations according to the present invention preferably comprise high molecular weight (i.e. 85,000–95,000 mass units) hydroxypropyl methylcellulose. It will be apparent to those skilled in the art that release by diffusion and erosion can occur simultaneously.
(b) In multiparticulate cores, the active compound is present in a number of particles which also contain adjuvants, diluents or carriers. Suitable adjuvants, diluents and carriers include microcrystalline cellulose (preferably having a nominal mean particle size of 50 µm) and lactose. Typically, the blended ingredients are formed into a wet mass which is extruded and spheronized to form beads which are then dried. The particles may then be filled into capsules. Prior to encapsulation, the particles can optionally be coated with a semipermeable or low solubility membrane [see (d) and (e) below].
(c) Impermeable coatings are applied to tablets containing the active compound. "Impermeable" means that no significant transport of the active compound can take place across the coating during the intended release period of the formulation, although water can pass through. Suitable materials include film-forming polymers and waxes [e.g. thermoplastic polymers such as poly(ethylene-covinyl acetate), poly(vinyl chloride), ethyl cellulose and cellulose acetate] and the coating thickness is preferably greater than 100 µm. The aperture may be formed by drilling, or if the coated formulation is conical, by cutting off the tip.
(d) Coatings of low aqueous solubility include polymers. The solubility of such polymers may be pH-dependent, for example substantially insoluble at pH<5 (so that dissolution does not take place in the stomach) and water soluble at pH>5. Preferred pH-sensitive polymers include shellac, phthalate derivatives (including cellulose acetate phthalate, polyvinylacetate phthalate), polyacrylic acid derivatives, and vinyl acetate and crotonic acid copolymers.
(e) Semipermeable membrane coatings allow the active compound to diffuse across the membrane or through liquid filled pores within the membrane. Suitable coating materials include polymers such as cellulose ester or ether, and acrylic polymers. Preferred materials include ethyl cellulose, cellulose acetate and cellulose acetate butyrate.
(f) Resinates may be prepared by treating anionic ion exchange resin beads (for example sodium polystyrene sulphonate) with an acid addition salt of the active ingredient.
(g) Pulsatile devices have the capacity to release drug at various points of the gastrointestinal tract. They may depend on osmotic potential to trigger release (see U.S. Pat. No. 3,952,741) or erosion of polymeric material due to changes in pH or microbial degradation. Suitable polymeric materials include pectin [Rubinstein et al, 1991, Pectic salt as a colonic delivery system, Proceed. Intern. Symp. Control. Rel. Bioact. Mater.], methacrylategalactomannan [Lehman et al, 1991, Methacrylate-galactomannan coating for colonic specific drug delivery, ibid], matter containing azobonds [Kopeckova et al, 1991, Bioadhesive polymers for colon specific drug delivery, ibid], chondroitin [Sintov et al, 1991, Colonic administration of indomethacin using modified chondroitin in a cannulated dog model, ibid], dextran hydrogels [Bronsted et al, 1993, A novel hydrogel system designed for controlled drug delivery to the colon, ibid], methacrylic acid copolymers [Siefke et al, 1993, β-Cyclodextrin matrix films for colon specific drug delivery, ibid], and amylose [Milojevik et al, In vitro and in vivo evaluation of amylose coated pellets for colon specific drug delivery, ibid]. Delivery to specific points of the gastrointestinal tract may also be achieved using multilayered tablets [Gazzaniga et al, 1993, Time dependent oral delivery system for colon specific release, ibid], or hydrogel plugs in a capsule [Binns et al, Application of a pH-independent PEG-based hydrogel to afford pulsatile drug delivery].

Formulations wherein the 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof, is embedded in a matrix from which it is released by diffusion or erosion, are of particular interest. Preferably, such formulations comprise 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof; one or more release rate modifiers; one or more organic acids; and one or more tabletting excipients.

Release rate modifiers that may be mentioned include hydroxypropylmethyl cellulose, methyl cellulose, sodium carboxymethylcellulose, ethyl cellulose, cellulose acetate, polyethylene oxide, xanthan gum, carbomer, ammonio methacrylate copolymer, hydrogenated castor oil, carnauba wax, paraffin wax, cellulose acetate phthalate, hydroxypropylmethyl cellulose phthalate and methacrylic acid copolymer. Hydroxypropylmethyl cellulose is of particular interest.

Preferred hydroxypropylmethyl celluloses have one or preferably more than one of the following features:
- a number average molecular weight in the range of about 20,000 to about 250,000, such as 20,000 to 125,000, more especially 25,000 to 100,000 (for example 27,000 or 89,000)
- a degree of methyl substitution in the range of about 15% to about 35%, such as 19–30% (for example 19–24%)
- a degree of hydroxy substitution in the range of about 2% to about 15%, such as 4–12% (for example 7–12%)
- the nominal viscosity of a 2% aqueous solution lies in the range of about 50 to about 150,000 cps, such as 50 to 100,000 cps, more especially 50 to 15,000 cps (for example 75 to 5,000 cps).

A number of hydroxypropylmethyl cellulose polymers are available commercially under the brand name Methocel™, and some of those suitable for use in formulations according to the invention are given in the table that follows:

| Methocel ™ grade | Number average MW | Degree of methyl substitution | Degree of hydroxy substitution | Nominal viscosity of a 2% aqueous solution | USP designation |
|---|---|---|---|---|---|
| K4M | 89,000 | 19–24% | 7–12% | 4,000 cps | 2208 |
| K15M | 125,000 | " | " | 15,000 cps | " |
| K100M | 215,000 | " | " | 100,000 cps | " |
| K100LV | 27,000 | " | " | 100 cps | " |
| E4M | 93,000 | 28–30% | 7–12% | 4,000 cps | 2910 |
| E10M | 113,000 | " | " | 10,000 cps | " |
| F4M | 90,000 | 27–30% | 4–7.5% | 4,000 cps | 2906 |

Methocel ™ K100LV, and especially K4M, have characteristics of particular interest.

It will be apparent to those skilled in the art that the hydroxypropylmethyl cellulose may consist of molecules of different chain lengths, but that the average chain length gives a molecular weight in the range stated.

Tabletting excipients for use in formulations according to the invention may include diluents, such as lactose monohydrate and anhydrous calcium hydrogen phosphate, and lubricants, such as magnesium stearate.

Organic acids for use in formulations according to the invention are the pharmaceutically acceptable organic acids, or mixtures thereof, and may contain one or more carboxylic acid groups. Preferably, one or more of the organic acids has a pKa (or lower/lowest pKa, for di-/multicarboxylic acids) in the range of about 1.75 to about 5.5, such as 3.25–5.0, more especially 4.0–5.0 (for example 4.1–4.8).

Preferably, one or more of the organic acids present is selected from: adipic acid, ascorbic acid, aspartic acid, benzoic acid, citric acid, fumaric acid, glutamic acid, lactic acid, maleic acid, malic acid, mandelic acid, sorbic acid, succinic acid and tartaric acid.

More preferably one or more of the organic acids present is selected from: adipic acid, sorbic acid and succinic acid.

Preferably, just one organic acid is present. More preferably, the sole organic acid is adipic acid.

Preferably, the 4-amino-6,7-dimethoxy-2-(5-methanesulfonamido-1,2,3,4-tetrahydroisoquinol-2-yl)-5-(2-pyridyl)quinazoline, or the pharmaceutically acceptable salt thereof, makes up about 0.05% to about 25%, such as 0.5–20% (for example 1–15%) by weight of the formulation, expressed as free base.

Preferably, the hydroxypropylmethyl cellulose makes up about 10% to about 60%, such as 15–50%, more especially 20–40% (for example 22.5–30%) by weight of the formulation.

Preferably, about 5% to about 40%, such as 10–30% (for example 15–25%) by weight of the formulation is made up of organic acid.

Matrix tablet formulations according to the invention may be colour coated. The percentages given above relate to proportions in tablets prior to any optional coating being applied.

Therefore, in a particularly preferred aspect, the invention provides a controlled release matrix tablet formulation comprising 1–15% by weight of 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof, 15–50% by weight hydroxypropylmethyl cellulose, 5–15% by weight lactose monohydrate, 15–40% by weight anhydrous calcium hydrogen phosphate, 10–30% by weight adipic acid, and 0.5–2% magnesium stearate. Additionally, the matrix tablet may be provided with a colour coating (not taken into account in the above percentages).

The invention also provides a controlled-release pharmaceutical formulation for oral administration comprising 4-amino-6,7-dimethoxy-2-(5-methanesulfonamido-1,2,3,4-tetrahydroisoquinol-2-yl)-5-(2-pyridyl)quinazoline or a pharmaceutically acceptable salt thereof; hydroxypropylmethyl cellulose; one or more organic acids; and one or more tabletting excipients.

Formulations according to the invention, especially matrix formulations containing an organic acid, have the advantage that the rate of release of 4-amino-6,7-dimethoxy-2-(5-methanesulfonamido-1,2,3,4-tetrahydroisoquinol-2-yl)-5-(2-pyridyl)quinazoline therefrom in aqueous media is independent of the pH of the media. This is surprising, because 4-amino-6,7-dimethoxy-2-(5-methanesulfonamido-1,2,3,4-tetrahydroisoquinol-2-yl)-5-(2-pyridyl)quinazoline is a basic compound and so is expected to be more soluble (and hence to be released more rapidly) in acidic conditions (as found in the stomach) than in neutral conditions (as found in the lower portions of the gastrointestinal tract). However, in patients, the drug is not liberated all at once in the stomach, but is delivered along the length of the gastrointestinal tract. This leads to sustained release and prolonged action of the drug. Nevertheless, the formulations are very simple and so can be manufactured easily and at a comparatively low cost.

Therefore, the invention further provides such formulations characterized in that the rate at which the 4-amino-6, 7-dimethoxy-2-(5-methanesulfonamido-1,2,3,4-tetrahydroisoquinol-2-yl)-5-(2-pyridyl)quinazoline, or the pharmaceutically acceptable salt thereof, is released therefrom is substantially independent of the pH of the surroundings.

"Substantially independent of the pH of the surroundings" may be defined as meaning that when the release profile of a formulation is measured at pH 2 and pH 7.5, then the percentage of drug released at a certain time point following commencement of the dissolution test (for example 6 hours) does not differ under the two pH conditions by more than about 20%, such as not more than 15%, preferably not more than 10%, for example about 5%.

Preferably, the 4-amino-6,7-dimethoxy-2-(5-methanesulfonamido-1,2,3,4-tetrahydroisoquinol-2-yl)-5-(2-pyridyl)quinazoline is present as a pharmaceutically acceptable salt, such as its mesylate salt.

According to another aspect of the invention, there is provided the use of 4-amino-6,7-dimethoxy-2-(5-methanesulfonamido-1,2,3,4-tetrahydroisoquinol-2-yl)-5-(2-pyridyl)quinazoline, or a pharmaceutically acceptable salt thereof, in the manufacture of a medicament for the treatment of benign prostatic hyperplasia, characterized in that the medicament is a controlled-release pharmaceutical formulation as defined above.

There is also provided a method of treatment of benign prostatic hyperplasia which comprises administering an effective amount of a controlled-release pharmaceutical formulation as defined above, to a patient in need of such treatment.

The invention further provides a process for the production of a pharmaceutical formulation containing 4-amino-6, 7-dimethoxy-2-(5-methanesulfonamido-1,2,3,4-tetrahydroisoquinol-2-yl)-5-(2-pyridyl)quinazoline, or a pharmaceutically acceptable salt thereof; hydroxypropylmethyl cellulose; one or more organic acids; and one or more tabletting excipients; which comprises mixing the ingredients; followed by pressing into tablets.

P Artursson and J Karlsson described the use of monolayers of Caco-2 cells to generate apparent permeability coefficients (Papp values) for drug absorption across the intestinal epithelium in 'Correlation between oral drug absorption in humans and apparent drug permeability coefficients in human intestinal epithelial (Caco-2) cells', Biochemical and Biophysical Research Communications, Vol 175 (3), pp 880–885, 1991.

It has now been found that the absorption of α adrenergic receptor antagonist compounds, or pharmaceutically acceptable salts thereof, having Papp values less than $15 \times 10^{-6}$ cm/s, can be improved, and made more predictable, by delivering the majority of the compound to the upper gastrointestinal tract.

Thus, in a broader aspect, the invention may be described as a controlled-release pharmaceutical formulation for oral administration comprising an α adrenergic receptor antagonist compound, or a pharmaceutically acceptable salt thereof, the compound having a Papp value of less than $15 \times 10^{-6}$ cm/s across a monolayer of Caco-2 cells; and a pharmaceutically acceptable adjuvant, diluent or carrier; characterized in that the formulation is adapted to release at least 50% by weight of the α adrenergic receptor antagonist compound, or the pharmaceutically acceptable salt thereof, after 6 hours in Apparatus 1 described in the United States Pharmacopoeia 24 (2000), pp 1941–1943, having 1 litre vessels, baskets of 40 mesh (0.4 mm apertures), a rotation speed of 100 rpm, and a dissolution medium consisting of 900 ml of 0.01 M hydrochloric acid containing 0.7% w/v sodium chloride at 37° C.

Preferably, when measuring the Papp value, the initial concentration of test compound in the donor chamber is at a relevant therapeutic concentration, for example 25 μM. 4-Amino-6,7-dimethoxy-2-(5-methanesulfonamido-1,2,3,4-tetrahydroisoquinol-2-yl)-5-(2-pyridyl)quinazoline mesylate was tested at this concentration and found to have a Papp value of $11 \times 10^{-6}$ cm/s.

Besides 4-amino-6,7-dimethoxy-2-(5-methanesulfonamido-1,2,3,4-tetrahydroisoquinol-2-yl)-5-(2-pyridyl) quinazoline, and its pharmaceutically acceptable salts, silodosin [also known as KMD-3213; see Drugs of the Future (2001), 26(6), 553–560] is an α adrenergic receptor antagonist compound of interest.

BRIEF DESCRIPTION OF THE DRAWING

The invention is illustrated by the following examples with reference to the accompanying drawings in which.

The following abbreviations may be used:

| | |
|---|---|
| ATCC | American Type Culture Collection |
| HBSS | Hanks balanced salt solution |
| HPLC | high performance liquid chromatography |
| HPMC | hydroxypropylmethyl cellulose |
| LC-MS | liquid chromatography mass spectroscopy |
| MEM | minimum essential medium |
| Ph Eur | European Pharmacopoeia |
| SRC | standard round convex |

EXAMPLES 1–5

Tablet Formulations of 4-amino-6,7-dimethoxy-2-(5-methanesulfonamido-1,2,3,4-tetrahydroisoquinol-2-yl)-5-(2-pyridyl)quinazoline mesylate Containing Methocel™ K4M The following table shows the ingredients for preparing five tablet formulations containing, respectively, 1, 3, 6, 9 and 12 mg of active ingredient, expressed as free base.

| Ingredient (mg) (reference to standard) | Ex 1 | Ex 2 | Ex 3 | Ex 4 | Ex 5 |
|---|---|---|---|---|---|
| 4-amino-6,7-dimethoxy-2-(5-methanesulfonamido-1,2,3,4-tetrahydroisoquinol-2-yl)-5-(2-pyridyl)quinazoline mesylate (Pfizer) | 1.189[1] | 3.567 | 7.134 | 10.701 | 14.268 |
| HPMC (Methocel K4M, Ph.Eur) | 30.000 | 30.000 | 30.000 | 22.500 | 22.500 |
| Lactose Monohydrate (Ph.Eur) | 13.203 | 10.108 | 9.216 | 10.200 | 9.308 |
| Calcium Hydrogen Phosphate, Anhydrous (Ph.Eur) | 39.608 | 30.325 | 27.650 | 30.599 | 27.924 |
| Adipic Acid [DAB[2]] | 15.000 | 25.000 | 25.000 | 25.000 | 25.000 |
| Magnesium Stearate (Ph.Eur) | 1.000 | 1.000 | 1.000 | 1.000 | 1.000 |
| Tablet weight (mg) | 100.000 | 100.000 | 100.000 | 100.000 | 100.000 |

[1]Equivalent to 1.0 mg 4-amino-6,7-dimethoxy-2-(5-methanesulfonamido-1,2,3,4-tetrahydroisoquinol-2-yl)-5-(2-pyridyl)quinazoline, in the form of its free base
[2]DAB is the Deutsches Arzeibuch (German Pharmacopoeia)

Method

The adipic acid was first screened through a suitable screen (e.g. 500 micron). The lactose monohydrate, hydroxypropylmethyl cellulose, 4-amino-6,7-dimethoxy-2-(5-methanesulfonamido-1,2,3,4-tetrahydroisoquinol-2-yl)-5-(2-pyridyl)quinazoline mesylate, the screened adipic acid and calcium hydrogen phosphate, anhydrous were then added to a suitable blender (e.g. a tumble mixer) and blended. The blend was screened through a suitable screen (e.g. 500 micron) and reblended. About 50% of the lubricant (magnesium stearate) was screened, added to the blend and blended briefly.

The blend was roller compacted through a suitable roller compactor. The ribbon blend was then granulated, by screening through a suitable screen (e.g. 500 micron) and reblended. The remaining lubricant was screened, added to the blend and blended briefly.

The granules were then tabletted using appropriate 6 mm tooling to give 6 mm standard round convex white tablets with no engraving, which were then de-dusted.

EXAMPLES 6–8

Tablet Formulations of 4-amino-6,7-dimethoxy-2-(5-methanesulfonamido-1,2,3,4-tetrahydroisoquinol-2-yl)-5-(2-pyridyl)quinazoline mesylate Containing Methocel™ K100LV The following table shows the ingredients for preparing two tablet formulations containing, respectively, 9, 12 and 1 mg of active ingredient, expressed as free base.

| Ingredient (mg) (reference to standard) | Ex 6 | Ex 7 | Ex 8 |
|---|---|---|---|
| 4-amino-6,7-dimethoxy-2-(5-methanesulfonamido-1,2,3,4-tetrahydroisoquinol-2-yl)-5-(2-pyridyl)quinazoline mesylate (Pfizer) | 10.702[1] | 14.269 | 1.189 |
| HPMC (Methocel ™ K100LV, Ph.Eur) | 100.000 | 100.000 | 40.00 |
| Lactose Monohydrate (Ph.Eur) | 11.825 | 10.933 | 10.703 |
| Calcium Hydrogen Phosphate, Anhydrous (Ph.Eur) | 35.473 | 32.798 | 32.108 |
| Adipic Acid [DAB] | 40.000 | 40.000 | 15.000 |
| Magnesium Stearate (Ph.Eur) | 2.000 | 2.000 | 1.000 |
| Tablet weight (mg) | 200.000 | 200.000 | 100.000 |

Method

The tablets of Examples 6, 7 and 8 were prepared analogously to those of Examples 1 to 5. However, in Examples 6 and 7, 8 mm tooling was used so as to give 8 mm standard round convex white tablets.

EXAMPLE 9

Tablet Formulation of 4-amino-6,7-dimethoxy-2-(5-methanesulfonamido-1,2,3,4-tetrahydroisoquinol-2-yl)-5-(2-pyridyl)quinazoline mesylate Containing Methocel™ K100M The following table shows the ingredients for preparing a tablet formulation containing 3 mg of active ingredient, expressed as free base.

| Ingredient (mg) (reference to standard) | Ex 9 |
|---|---|
| 4-amino-6,7-dimethoxy-2-(5-methanesulfonamido-1,2,3,4-tetrahydroisoquinol-2-yl)-5-(2-pyridyl)quinazoline mesylate (Pfizer) | 3.567[1] |
| HPMC (Methocel K100M, Ph.Eur) | 40.000 |

-continued

| Ingredient (mg) (reference to standard) | Ex 9 |
|---|---|
| Lactose Monohydrate (Ph.Eur) | 7.608 |
| Calcium Hydrogen Phosphate, Anhydrous (Ph.Eur) | 22.825 |
| Adipic Acid [DAB] | 25.000 |
| Magnesium Stearate (Ph.Eur) | 1.000 |
| Tablet weight (mg) | 100.000 |

Method

The tablets of Example 9 were prepared analogously to those of Examples 1 to 5.

EXAMPLE 10

Dissolution Studies at Different pH

Figure 1:
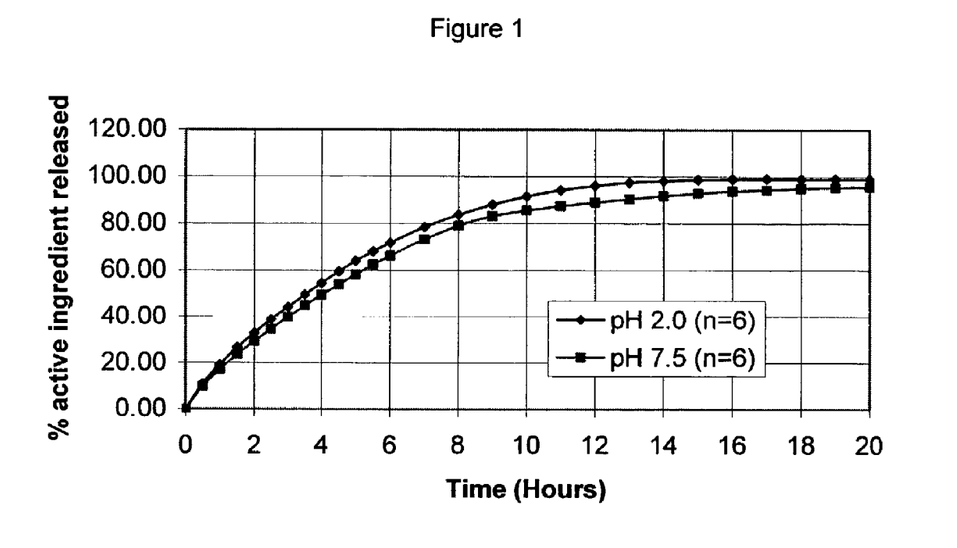
FIG. 1 shows the percentage of drug compound released v time from a formulation prepared according to Example 2 in a standard dissolution test under two different pH conditions.

The dissolution test according to United States Pharmacopoeia 24 (2000), pp 1941–1943, "Apparatus 1" (incorporated herein by reference) was followed, but using a covered vessel of nominal capacity 5000 ml (internal diameter 150 mm, height 345 mm). Formulations prepared according to Example 2 were dissolved in an aqueous buffer of pH 2 (composition 0.01M HCl and 0.12M NaCl) and in an aqueous buffer of pH 7.5 (composition 0.06M KCl, 0.03M NaCl, 0.006M $KH_2PO_4$ and 0.005M NaOH). The dissolution fluid volume was 3000 ml, the temperature was 37° C., the rotation speed of the baskets was 100 rpm, and the drug compound released was detected by UV spectroscopy at a wavelength of 246 nm. The percentage of active ingredient released v time is shown in FIG. 1.

It can be seen that the release profile at pH 2 and the release profile at pH 7.5 are almost identical, indicating that when administered orally to a patient the formulation is likely to deliver drug along the length of the gastrointestinal tract, leading to sustained release and prolonged drug action.

Figure 2:
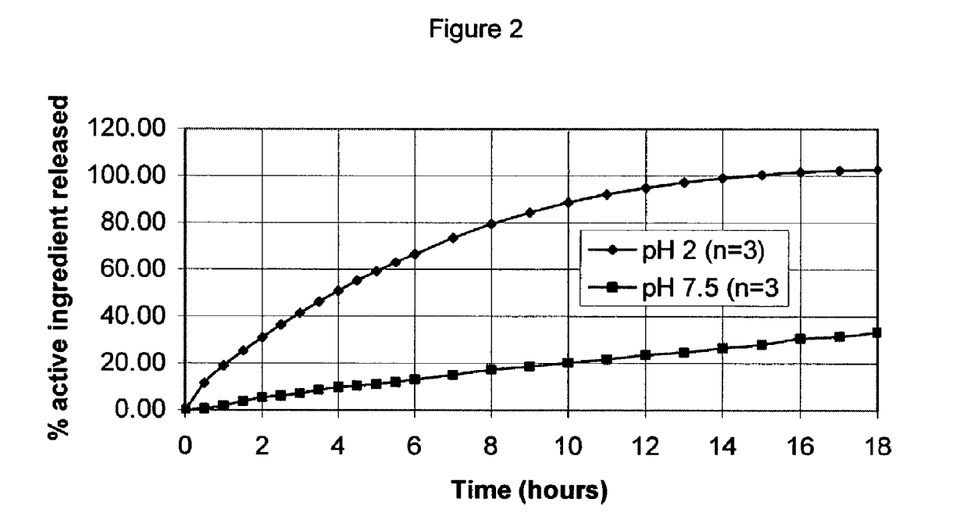
FIG. 2 shows, under corresponding test conditions, the percentage of drug compound released v time from a formulation analogous to that prepared according to Example 2, but containing no adipic acid.

For comparison, a formulation analogous to that of Example 2 was prepared, but which contained no adipic acid. The release profile of this formulation was measured at pH 2 and pH 7.5 as above and the percentage of drug compound released v time is shown in FIG. 2. It can be seen that the release profile at pH 2 and the release profile at pH 7.5 are very different. Accordingly this formulation is not likely to deliver drug along the length of the gastrointestinal tract, and hence give sustained release and prolonged drug action, when administered orally to a patient.

EXAMPLE 11

Modified Release Bead Formulation

The modified release bead (or multiparticulate) formulation consists of bead cores, coated with a release rate modifying membrane, filled into a hard gelatine capsule shell. The bead core composition is detailed in Table 1, the final dosage form is detailed in Table 2.

TABLE 1 bead core ingredients

| Ingredient | Specification | Weight (mg) |
|---|---|---|
| 4-amino-6,7-dimethoxy-2-(5-methanesulfonamido-1,2,3,4-tetrahydroisoquinol-2-yl)-5-(2-pyridyl)quinazoline mesylate[a] | Pfizer | 1.189 |
| Lactose monohydrate[b] | Ph. Eur/NF | 73.811 |
| Adipic acid | DAB | 15.000 |
| Microcrystalline cellulose[c] | Ph. Eur/NF | 10.000 |
| Water, Purified[d] | Ph. Eur | (26.000) |
| | | 100.000 |

[a]equivalent to 1.000 mg 4-amino-6,7-dimethoxy-2-(5-methanesulfonamido-1,2,3,4-tetrahydroisoquinol-2-yl)-5-(2-pyridyl)quinazoline calculated on a theoretical activity of 84.1%
[b]as Pharmatose 110 M (particle size specification 0–20% less than 63 μm, 30–60% less than 100 μm, 75–90% less than 150 μm, 100% less than 315 μm)
[c]as Avicel ™ PH101
[d]Removed during the drying step, does not appear in the final product.

TABLE 2 modified release bead ingredients

| Ingredient | Specification | mg/unit |
|---|---|---|
| 4-amino-6,7-dimethoxy-2-(5-methanesulfonamido-1,2,3,4-tetrahydroisoquinol-2-yl)-5-(2-pyridyl)quinazoline[a] core beads | Pfizer | 100.000 |
| Ammonio Methacrylate Copolymer, Type B[b] | USP/NF. | 16.200 |
| Ammonio Methacrylate Copolymer, Type A[c] | USP/NF | 1.800 |
| Talc | Ph. Eur | 9.000 |
| Triethyl Citrate | USP/NF | 3.600 |
| Water, Purified[d] | Ph. Eur | (147.400) |
| Talc[e] | Ph. Eur | (5.000) |
| Total | | 130.600 |
| Size 4 white opaque hard gelatine capsule shell | | |

[a]equivalent to 1.000 mg 4-amino-6,7-dimethoxy-2-(5-methanesulfonamido-1,2,3,4-tetrahydroisoquinol-2-yl)-5-(2-pyridyl)quinazoline
[b]as Eudragit ™ RS30D. Equivalent to 54 g Eudragit ™ RS30D, an aqueous dispersion with a solids content of 30% w/w.
[c]as Eudragit ™ RL30D. Equivalent to 6 g Eudragit ™ RL30D, an aqueous dispersion with a solids content of 30% w/w
[d]the water content is lost during the process and does not appear in the final product.
[e]this talc is applied during processing to aid lubrication and is removed by sieving.

Manufacturing Process

Bead cores were manufactured by extrusion & spheronisation. The ingredients listed in Table 1 were first blended using a blend-screen-blend process. The blend was then wet-granulated using a Peerless EG2 mixer. The resulting wet mass was then extruded through a Nica™ 140 extruder (aperture size 1.0 mm), followed by spheronisation in a Caleva™ spheroniser. The resulting cores were tray dried in an oven at 40° C. for 22 hours.

A polymer dispersion was then coated onto the bead cores (size between 850 µm and 1.40 mm). The dispersion was prepared by mixing Eudragit™ RS30D and Eudragit™ RL30D polymers, talc and triethyl citrate. Water was also added to obtain a solids content of about 14%. Coating-runs were performed using a fluidised bed Strea coater with the Wurster column in place, at a rate of about 6 g/min, with an inlet air temperature of 40° C., an atomizing air pressure of 0.8 bar ($8 \times 10^4$ N/m$^2$), a fluidizing air setting of 4, a tubing size of 0.093" ID×0.062" wall (2.3 mm×1.6 mm) and a nozzle size of 1 mm. After coating, coated cores were mixed with 5% talc and allowed to cure at 40° C. for 31 hours. After curing, the talc was removed by sieving. The coated bead cores were then loaded into capsules (130.600 mg per capsule)

EXAMPLE 12

Osmotic Tablet Formulation

A modified release osmotic formulation consisting of a bilayer tablet core, with an impermeable coat (as described above) having orifices in it to enable drug release was prepared using the ingredients listed in Table 3 (tablet core composition) and Table 4 (final dosage form) below.

TABLE 3 osmotic tablet core composition

| Ingredient | Weight (mg/unit) |
| --- | --- |
| Layer 1: | |
| 4-amino-6,7-dimethoxy-2-(5-methanesulfonamido-1,2,3,4-tetrahydroisoquinol-2-yl)-5-(2-pyridyl)quinazoline (free base) | 10.000 |
| Xylitab ™ 200[d] | 92.000 |
| Polyethylene oxide[a] | 88.000 |
| Sodium starch glycolate[b] | 8.000 |
| Magnesium stearate | 2.000 |
| Layer 2: | |
| Sodium starch glycolate[b] | 37.200 |
| Silicified microcrystalline cellulose[c] | 12.400 |
| Colouring (FD&C red #40) | 0.250 |
| Magnesium stearate | 0.150 |
| Total | 250.000 mg |
| Tablet shape: 11/32" (8.7 mm) SRC | |

[a]as Polyox ™ WSR-205
[b]as Explotab ™
[c]as Prosolv ™ SMCC 90
[d]a mixture of xylitol (minimum 96.5%) and carboxymethyl cellulose sodium (maximum 2.0%), manufactured by Danesco sweeteners

TABLE 4 modified release osmotic composition

| Ingredient | Weight (mg/unit) |
| --- | --- |
| 4-amino-6,7-dimethoxy-2-(5-methanesulfonamido-1,2,3,4-tetrahydroisoquinol-2-yl)-5-(2-pyridyl)quinazoline tablet core[a] | 250.000 |
| Cellulose acetate[b] | 16.975 |
| Polyethylene glycol[c] | 7.275 |
| Total | 274.250 |

Description:
11/32" (8.7 mm) SRC bilayer film coated tablet with 5 × 900 µm holes in the drug face

[a]as detailed in Table 1
[b]as manufactured by Eastman, type CA 398-10
[c]having a nominal average molecular weight of 3350

Manufacturing Process

Bilayer tablet cores were manufactured via compression of two dry powder blends. Firstly, the excipients of Layer 1 (except magnesium stearate) were blended with 4-amino-6,7-dimethoxy-2-(5-methanesulfonamido-1,2,3,4-tetrahydroisoquinol-2-yl)-5-(2-pyridyl)quinazoline, then screened through a suitable sieve, and blended again. The excipients of Layer 2 (except magnesium stearate) were also blended together, then screened through a suitable sieve and blended again. The lubricant magnesium stearate was then mixed into each blend. Both blends were then compressed together using a suitable tablet press, to form a bilayer tablet.

A film coat was applied to the tablets by spraying a polymer solution onto the tablet cores. The solution was prepared by mixing cellulose acetate, polyethylene glycol, water and acetone. Coating runs were performed using a suitable pan coater. After coating, 5×900 µm holes were drilled through the coat on the drug face of the tablet.

EXAMPLE 13

Dissolution Studies

A number of the formulations from the preceding Examples were tested in the dissolution test according to United States Pharmacopoeia 24 (2000), pp 1941–1943, "Apparatus 1", using 1 litre vessels, baskets of 40 mesh (0.4 mm apertures), a rotation speed of 100 rpm, and a dissolution medium consisting of 900 ml of 0.01 M hydrochloric acid (pH 2) containing 0.7% w/v sodium chloride at 37° C. (unless otherwise shown). The percentage of drug compound released was detected by UV spectroscopy at a wavelength of 246 nm, and is shown in the following table.

Results

| Time (h) | Ex 1 '1 mg 9 h' n = 6[c] | Ex 2 '3 mg 9 h' n = 6 | Ex 3 '6 mg 9 h' n = 6 | Ex 4 '9 mg 9 h' n = 6 | Ex 8 '1 mg 6 h' n = 6 | Ex 9 '3 mg 15 h' n = 6 | Ex 11[a] Bead n = 3 | Ex 12[b] Osmotic n = 3 |
|---|---|---|---|---|---|---|---|---|
| 0.0 | 0.00 | 0.00 | 0.00 | 0.00 | 0.00 | 0.00 | 0.00 | 0.00 |
| 1.0 | 24.00 | 20.00 | 15.00 | 16.00 | 27.00 | 16.00 | 5.00 | — |
| 2.0 | 39.00 | 34.00 | 26.00 | 27.00 | 48.00 | 26.00 | 9.00 | 38.00 |
| 3.0 | 52.00 | 45.00 | 36.00 | 37.00 | 66.00 | 35.00 | 23.00 | — |
| 4.0 | 64.00 | 56.00 | 46.00 | 47.00 | 83.00 | 43.00 | 43.00 | 67.00 |
| 5.0 | 75.00 | 65.00 | 55.00 | 55.00 | 91.00 | 51.00 | 61.00 | — |
| 6.0 | 83.00 | 73.00 | 63.00 | 63.00 | 96.00 | 58.00 | 77.00 | — |
| 7.0 | 92.00 | 80.00 | 70.00 | 70.00 | 97.00 | 64.00 | 83.00 | — |
| 8.0 | 98.00 | 86.00 | 77.00 | 77.00 | — | 70.00 | 88.00 | 97.00 |
| 9.0 | 102.00 | 91.00 | 83.00 | 83.00 | — | 75.00 | 91.00 | — |
| 10.0 | 107.00 | — | 87.00 | 88.00 | — | 80.00 | 93.00 | — |
| 11.0 | — | — | 92.00 | 92.00 | — | 84.00 | 95.00 | — |
| 12.0 | — | — | 95.00 | 96.00 | — | 88.00 | 96.00 | — |
| 13.0 | — | — | 98.00 | 98.00 | — | 91.00 | 97.00 | — |
| 14.0 | — | — | 99.00 | 101.00 | — | 93.00 | 98.00 | 98.00 |
| 15.0 | — | — | 101.00 | 101.00 | — | 95.00 | 99.00 | — |

Notes:
[a] dissolution volume 1000 ml instead of 900 ml
[b] dissolution medium was changed to 0.035 M NaCl, 0.026 M $KH_2PO_4$, 0.064 M KCl (pH 7.5 instead of pH 2) during the experiment, at 2 hours. In view of the low solubility of the drug at pH 7.5, drug release could not be measured directly. Therefore, at subsequent time points, one of the tablets was assayed for residual drug by dissolving in a recovery solution (pH 2) and analyzing the solution by UV spectroscopy at a wavelength of 246 nm and the amount of drug released calculated.
[c] "n" values indicate the number of formulations tested to give a mean result

EXAMPLE 14

In Vivo Studies

A number of the formulations from the preceding Examples were administered to human subjects. Blood samples were taken at various time points and the concentration of the drug in the plasma measured using HPLC followed by fluorescence detection. The cumulative percentage of drug absorbed was then estimated by deconvolution of the data, using a solution dose as a reference. The results are shown in the following table.

The results show that the formulations of the invention have good bioavailability, and have a smooth, sustained release profile suitable for once daily dosing.

EXAMPLE 15

Measurement of Papp Values

Caco-2 cells originating from a human colon carcinoma were obtained from the ATCC (HTB-37) and were used between passage number 24–44. Cells were maintained in MEM with Earles salts containing 2 mM L-glutamine, 1 mM

| Time (h) | Ex1 '1 mg 9 h' n = 16[a] | Ex 2 '3 mg 9 h' n = 16 | Ex 3 '6 mg 9 h' n = 15 | Ex 4 '9 mg 9 h' n = 15 | Ex 8 '1 mg 6 h' n = 16 | Ex 9 '3 mg 15 h' n = 16 |
|---|---|---|---|---|---|---|
| 0.0 | 0.000 | 0.000 | 0.000 | 0.000 | 0.000 | 0.000 |
| 0.5 | 11.265 | 10.412 | 12.331 | 11.931 | 15.042 | 10.168 |
| 1.0 | 20.055 | 19.701 | 12.331 | 11.931 | 26.152 | 20.705 |
| 2.0 | 35.361 | 42.634 | 25.977 | 31.243 | 45.840 | 23.246 |
| 3.0 | 43.499 | 49.403 | 31.113 | 41.141 | 58.511 | 35.610 |
| 4.0 | 59.187 | 60.685 | 44.658 | 51.640 | 74.125 | 35.610 |
| 6.0 | 60.449 | 60.685 | 45.721 | 55.536 | 74.125 | 38.239 |
| 8.0 | 60.792 | 61.948 | 48.387 | 55.755 | 74.125 | 39.210 |
| 10.0 | 62.381 | 61.948 | 50.004 | 56.054 | 74.125 | 39.754 |
| 12.0 | 62.381 | 61.948 | 50.017 | 56.054 | 74.125 | 40.636 |
| 15.0 | 63.570 | 61.948 | 51.718 | 56.054 | 74.125 | 40.636 |
| 18.0 | 63.989 | 62.985 | — | — | 74.125 | 41.780 |
| 24.0 | 70.099 | 68.967 | 57.323 | 62.932 | 79.591 | 47.020 |

Notes:
[a] n values indicate the number of patients receiving the formulation sodium pyruvate, 1% (v/v) MEM non-essential amino acids (Gibco) and 20% foetal calf serum (Sigma) at 37° C. in an atmosphere of 5% $CO_2$ and 90% relative humidity. Falcon 24 well filter inserts (Becton Dickinson) were seeded with $4 \times 10^4$ cells/well. The medium was changed every 2–3 days. The cells formed confluent, differentiated cell monolayers after 15 days and were used for transport studies between days 15–25.

The Caco-2 cells are grown on the filter supports to produce a monolayer with well defined and developed tight junctions. Mannitol is used in all experiments to monitor monolayer integrity and only monolayers with a mannitol flux rate $<1 \times 10^{-6}$ cm/sec were used in these studies.

Transport studies were conducted in triplicate wells using drug concentrations of 25 μM or lower in HBSS (Gibco). Test compounds were prepared as 25 micromolar solutions and 250 μl aliquots added to the apical chamber while 1 ml of HBSS was added to the basolateral chamber. The wells were incubated at 37° C. on a Denley Wellmixx plate shaker and samples were removed from both the apical and basolateral chamber after 2 hours and assayed for drug content using LC-MS.

Transport data across the Caco-2 cell monolayers is expressed as Papp values. Papp values are calculated according to the equation disclosed by Artursson and Karlsson as follows:

$Papp=(dQ/dt)(1/AC_0)$, wherein $dQ/dt$ is the permeability rate, $C_o$ the initial concentration in the donor chamber, and A the surface area of the monolayer.

When the starting concentration was 25 μm, 4-amino-6,7-dimethoxy-2-(5-methanesulfonamido-1,2,3,4-tetrahydroisoquinol-2-yl)-5-(2-pyridyl)quinazoline mesylate was found to have a Papp value of $11 \times 10^{-6}$ cm/s.

The invention claimed is:

1. A controlled-release pharmaceutical formulation for oral administration comprising 4-amino-6,7-dimethoxy-2-(5-methanesulfonamido-1,2,3,4-tetrahydroisoquinol-2-yl)-5-(2-pyridyl)quinazoline or a pharmaceutically acceptable salt thereof; about 22.5% to about 40% by weight hydroxypropylmethylcellulose; about 25% by weight adipic acid; about 7.6% to about 10.2% by weight lactose monohydrate; about 22.8% to about 30.6% by weight anhydrous calcium hydrogen phosphate; 1% by weight magnesium stearate; and a pharmaceutically acceptable adjuvant, diluent or carrier; characterized in that the formulation is adapted to release at least 50% by weight of the 4-amino-6,7-dimethoxy-2-(5-methanesulfonamido-1,2,3,4-tetrahydroisoquinol-2-yl)-5-(2-pyridyl)quinazoline or the pharmaceutically acceptable salt thereof, after six hours, at least 30% by weight after 3 hours, and less than 30% by weight after one hour, in Apparatus 1 described in the United States Pharmacopoeia 24 (2000), pp 1941–1943, having 1 litre vessel, baskets of 40 mesh (0.4 mm apertures), a rotation speed of 100 rpm, and a dissolution medium consisting of 900 ml of 0.01 M hydrochloric acid containing 0.7% w/v sodium chloride at 37° C. wherein the hydroxypropylmethyl cellulose has a number average molecular weight in the range 20,000–250,000, has a degree of methyl substitution in the range of about 15% to about 35%, has a degree of hydroxy substitution in the range of about 2% to about 15% and wherein the nominal viscosity of a 2% aqueous solution of the hydroxypropylmethylcellulose lies in the range of about 50 to about 150,000 cps.

2. A controlled release pharmaceutical formulation for oral administration comprising 4-amino-6,7-dimethoxy--2-(5-methanesulfonamido-1,2,3,4-tetrahydroisoquinol-2yl)-5-(2-pyridyl)quinazoline or a pharmaceutically acceptable salt thereof; about 22.5 to about 40% by weight hydroxypropylmethylcellulose; about 25% by weight adipic acid; about 7.6% to about 10.2% by weight lactose monohydrate; about 22.8% to about 30.6% by weight anhydrous calcium hydrogen phosphate; 1% by weight magnesium stearate; and a pharmaceutically acceptable adjuvant, diluent or carrier; characterized in that the formulation is adapted to release at least 50% by weight of the 4-amino-6,7-dimethoxy-2-(5-methanesulfonamido-1,2,3,4-tetrahydroisoquinol-2-yl)-5-(2-pyridyl)quinazoline or the pharmaceutically acceptable salt thereof, in the upper gastrointestinal tract of a patient wherein the hydroxypropylmethyl cellulose has a number average molecular weight in the range 20,000–250,000, has a degree of methyl substitution in the range of about 15% to about 35%, has a degree of hydroxy substitution in the range of about 2% to about 15% and wherein the nominal viscosity of a 2% aqueous solution of the hydroxypropylmethylcellulose lies in the range of about 50 to about 150,000 cps.

3. A formulation as claimed in claim 2, which contains from 0.1 to 20 mg of 4-amino-6,7-dimethoxy-2-(5methanesulfonamido-1,2,3,4-tetrahydroisoquinol-2-yl)-5-(2-pyridyl) quinazoline or the pharmaceutically acceptable salt thereof.

4. A formulation as claimed in claim 2, wherein the 4-amino-6,7-dimethoxy-2-(5-methanesulfonamido-1,2,3,4-tetrahydroisoquinol-2-yl)-5-(2-pyridyl)quinazoline or the pharmaceutically acceptable salt thereof, in said dosage form is:
   (a) embedded in a matrix from which it is released by diffusion or erosion;
   (b) present in a multiparticulate core;
   (c) released through an aperture provided in an impermeable coating;
   (d) released through a coating of low aqueous solubility;
   (e) released through a semipermeable coating;
   (f) present as an ion exchange resin; or
   (g) released at specific points in the gastrointestinal tract by a pulsatile device.

5. A formulation as claimed in claim 4, wherein the 4-amino-6,7-dimethoxy-2-(5-methanesulfonamido-1,2,3,4-tetrahydroisoquinol-2-yl)-5-(2-pyridyl)quinazoline or the pharmaceutically acceptable salt thereof, is embedded in a matrix from which it is released by diffusion or erosion.

6. A formulation as claimed in claim 5, wherein the 4-amino-6,7-dimethoxy-2-(5-methanesulfonamido-1,2,3,4-tetrahydroisoquinol-2yl)-5-(2-pyridyl)quinazoline or the pharmaceutically acceptable salt thereof, makes up about 0.05% to about 25% by weight of the formulation, expressed in the form of its free base.

7. A formulation as claimed in claim 5, characterized in that the rate at which the 4-amino-6,7-dimethoxy-2-(5-methanesulfonamido-1,2,3,4-tetrahydroisoquinol-2-yl)-5-(2-pyridyl)quinazoline or the pharmaceutically acceptable salt thereof, released therefrom is substantially independent of the pH of the surroundings.

8. A controlled release matrix tablet formulation comprising 1–15% by weight of 4-amino-6,7-dimethoxy-2-(5-methanesulfonamido-1,2,3,4-tetrahydroisoquinol-2-yl)-5-(2-pyridyl)quinazoline or a pharmaceutically acceptable salt thereof, 22.5–40% by weight hydroxypropylmethyl cellulose, 7.6–10.2% by weight lactose monohydrate, 22.8–30.6% by weight anhydrous calcium hydrogen phosphate, 25% by weight adipic acid, and 1% magnesium stearate wherein the hydroxypropylmethyl cellulose has a number average molecular weight in the range 20,000–250, 000, has a degree of methyl substitution in the range of about 15% to about 35%, has a degree of hydroxy substitution in the range of about 2% to about 15% and wherein the nominal viscosity of a 2% aqueous solution of the hydroxypropylmethylcellulose lies in the range of about 50 to about 150,000 cps.

9. A formulation as claimed in claim 2, wherein the 4-amino-6,7-dimethoxy-2-(5-methanesulfonamido-1,2,3,4-tetrahydroisoquinol-2-yl)-5-(2-pyridyl)quinazoline is present as its mesylate salt.

10. A method of treatment of benign prostatic hyperplasia, which comprises administering a formulation as defined in claim 2 to a patient in need of such treatment.

11. A controlled-release pharmaceutical formulation for oral administration comprising 4-amino-6,7-dimethoxy-2-(5-methanesulfonamido1,2,3,4-tetrahydroisoquinol-2-yl)-5-(2-pyridyl)quinazoline, or a pharmaceutically acceptable salt thereof, about 22.5% to about 40% by weight hydroxypropylmethylcellulose; about 25% by weight adipic acid; about 7.6% to about 10.2% by weight lactose monohydrate; about 22.8% to about 30.6% by weight anhydrous calcium hydrogen phosphate 1% by weight magnesium stearate; the compound having a Papp value of less than $15 \times 10^{-6}$ cm/s across a monolayer of Caco-2 cells; and a pharmaceutically acceptable adjuvant, diluent or carrier; characterized in that the formulation is adapted to release at least 50% by weight of 4-amino-6,7-dimethoxy-2-(5-methanesulfonamido-1,2,3,4-tetrahydroisoquinol-2-yl)-5-(2pyridyl)quinazoline, or the pharmaceutically acceptable salt thereof, after 6 hours in Apparatus 1 described in the United States Pharmacopoeia 24 (2000), pp 1941–1943, having 1 litre vessels, baskets of 40 mesh (0.4 mm apertures), a rotation speed of 100 rpm, and a dissolution medium consisting of 900 ml of 0.01 M hydrochloric acid containing 0.7% w/v sodium chloride at 37° C. wherein the hydroxypropylmethyl cellulose has a number average molecular weight in the range 20,000–250,000, has a degree of methyl substitution in the range of about 15% to about 35%, has a degree of hydroxy substitution in the range of about 2% to about 15% and wherein the nominal viscosity of a 2% aqueous solution of the hydroxypropylmethylcellulose lies in the range of about 50 to about 150,000 cps.

* * * * *